United States Patent
Meister (10) Patent No.: US 9,878,157 B2
(45) Date of Patent: Jan. 30, 2018

(54) PATIENT SPECIFIC FREQUENCY MODULATION ADAPTION

(71) Applicant: MED-EL Elektromedizinische Geraete GmbH, Innsbruck (AT)

(72) Inventor: Dirk Meister, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/251,281

(22) Filed: Aug. 30, 2016

(65) Prior Publication Data

US 2017/0056657 A1    Mar. 2, 2017

Related U.S. Application Data (60) Provisional application No. 62/212,645, filed on Sep. 1, 2015.

(51) Int. Cl.
*A61N 1/00* (2006.01)
*A61N 1/36* (2006.01)

(52) U.S. Cl.
CPC ..... *A61N 1/36032* (2013.01); *A61N 1/36036* (2017.08)

(58) Field of Classification Search
CPC ........................ A61N 1/36032; A61N 1/36036
See application file for complete search history.

(56) References Cited

U.S. PATENT DOCUMENTS

| | | | |
|---|---|---|---|
| 8,489,194 B2 * | 7/2013 | Meister | A61N 1/36036 381/320 |
| 2009/0264961 A1 | 10/2009 | Schleich et al. | |
| 2010/0204755 A1 | 8/2010 | Meister | |
| 2012/0004706 A1 | 1/2012 | Meister et al. | |
| 2013/0103396 A1 | 4/2013 | Swanson et al. | |

(Continued)

OTHER PUBLICATIONS

Haghparast et al., "Real-Time Pitch-Shifting of Musical Signals by a Time-Varying Factor Using Normalized Filtered Correlation Time-Scale Modification (NFC-TSM)," Proc. of the $10^{th}$ Int. Conference on Digital Audio Effects (DAFx-07), Bordeaux, France, pp. DAFX-1-DAFX-7, Sep. 10-15, 2007.

(Continued)

*Primary Examiner* — George Manuel
(74) *Attorney, Agent, or Firm* — Sunstein Kann Murphy & Timbers LLP (57) ABSTRACT

An input sound signal is processed to generate band pass signals that each represent an associated band of audio frequencies. Stimulation timing signals are generated for each band pass signal, including for one or more selected band pass signals using a timing function defined to determine a mapped instantaneous frequency by adjusting instantaneous frequency based on a frequency relation factor representing a relationship between: (1) the range of audio frequencies for the band pass channel, and (2) a patient-specific, channel-specific range of stimulation rates defined based on patient-specific pitch perception measurements to enhance patient pitch perception within the range of audio frequencies for the band pass channel, and iii. generate the stimulation timing signal for the selected band pass signal at the mapped instantaneous frequency of the selected band pass signal.

23 Claims, 11 Drawing Sheets

(56) References Cited

U.S. PATENT DOCUMENTS

| | | |
|---|---|---|
| 2013/0231714 A1 | 9/2013 | Harczos |
| 2014/0005746 A1 | 1/2014 | Schleich et al. |
| 2014/0058478 A1 | 2/2014 | Frühauf et al. |
| 2015/0080980 A1 | 3/2015 | Meister et al. |

OTHER PUBLICATIONS

Juillerat et al., "Low Latency Audio Pitch Shifting in the Time Doman," ICALIP, Shanghai, China, pp. 29-35, 2008.

Middlebrooks et al., "Selective Electrical Stimulation of the Auditory Nerve Activates a Pathway Specialized for High Temporal Acuity," The Journal of Neuroscience, vol. 30, No. 5, pp. 1937-1946, Feb. 3, 2010.

Nie et al., "Encoding Frequency Modulation to Improve Cochlear Implant Performance in Noise," IEEE Transactions on Biomedical Engineering, vol. 52, No. 1, pp. 64-73, Jan. 2005.

International Searching Authority, International Search Report—International Application No. PCT/US16/49398, dated Nov. 14, 2016, together with the Written Opinion of the International Searching Authority, 14 pages.

\* cited by examiner

PATIENT SPECIFIC FREQUENCY MODULATION ADAPTION

This application claims priority from U.S. Provisional Patent Application 62/212,645, filed Sep. 1, 2015, which is incorporated herein by reference in its entirety.

FIELD OF THE INVENTION

The present invention relates to hearing implant systems, and more specifically, to techniques for producing electrical stimulation signals in such systems.

BACKGROUND ART

Figure 1:
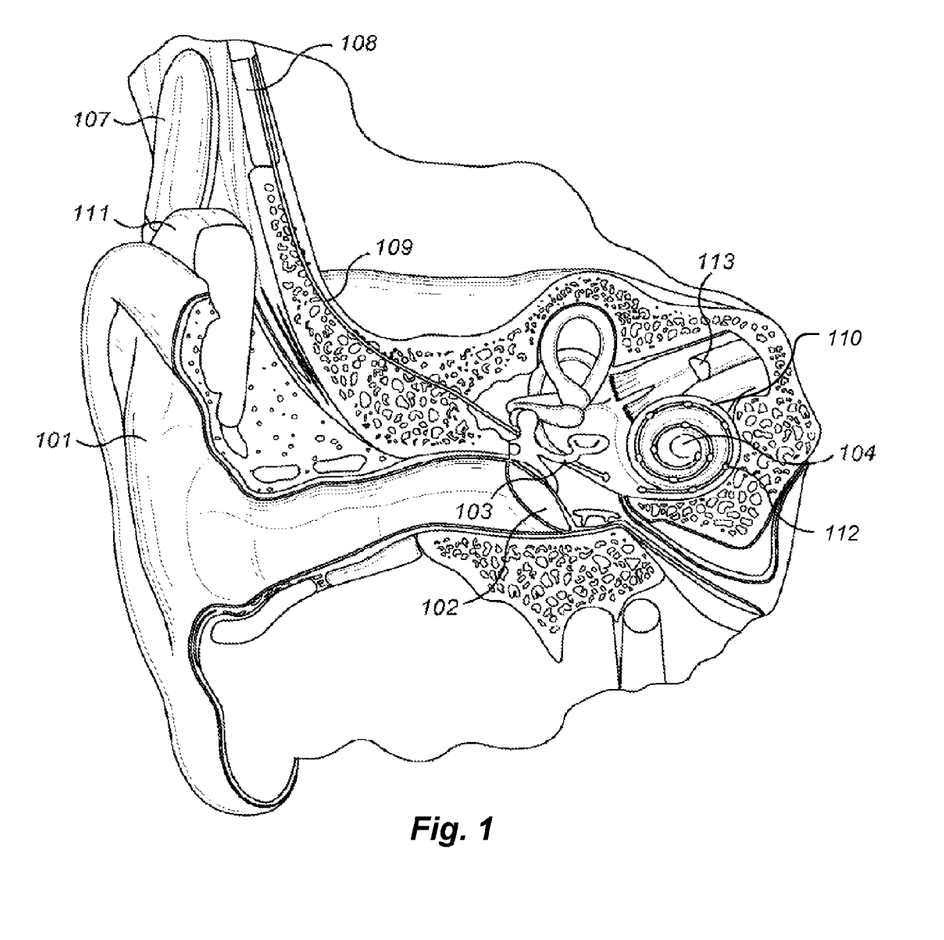
FIG. 1 shows a section view of a human ear with a typical cochlear implant system designed to deliver electrical stimulation to the inner ear.

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

Many cochlear implant coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

It is known that persons with normal hearing can discriminate between pitches with differences as small as 0.2%; see, e.g., Fastl, H., and M. Weinberger. "Frequency discrimination for pure and complex tones." *Acta Acustica united with Acustica* 49.1 (1981): 77-88; which is incorporated herein by reference in its entirety. On the other hand, discrimination of synthetic complex tones for well performing cochlear implant users is more in the range of two semi tones (one semi tone equals 6%); see, e.g., Ping, Lichuan, Meng Yuan, and Haihong Feng. "Musical pitch discrimination by cochlear implant users." *Annals of Otology, Rhinology & Laryngology* 121.5 (2012): 328-336; which is incorporated herein by reference in its entirety.

In addition, rate pitch perceptions for cochlear implant users can extend over a relatively high frequency range, higher than the stimulation rates typically applied in a given stimulation channel; see, e.g., Kong, Ying-Yee, and Robert P. Carlyon. "Temporal pitch perception at high rates in cochlear implants." *The Journal of the Acoustical Society of America* 127.5 (2010): 3114-3123; which is incorporated herein by reference in its entirety.

Middlebrooks, John C., and Russell L. Snyder. "Selective electrical stimulation of the auditory nerve activates a pathway specialized for high temporal acuity." *The Journal of Neuroscience* 30.5 (2010): 1937-1946 (incorporated herein by reference in its entirety) found that the neurons in the inferior colliculus that are responsible for coding low frequencies phase lock up to higher frequencies than those neurons that are responsible for the coding of higher frequencies.

Measurements of rate discrimination performance in cochlear implant users has shown individual- and electrode-specific results. The rate discrimination performance can in some cases even be better at higher rates than for lower rates; see, e.g., FIG. 3, subject C3 of Kong, Ying-Yee, et al. "Limits of temporal pitch in cochlear implants." *The Journal of the Acoustical Society of America* 125.3 (2009): 1649-1657 (incorporated herein by reference in its entirety).

Although the significance of the temporal fine structure information present in the input sound signal has been acknowledged for a long time, only a few stimulation schemes in commercially available cochlear implants are actually able to present this information to cochlear implant users. The Med-El FSP and FS4 coding strategies apply stimulation with a fixed frequency range depending on a band pass filter of the input signal. The frequency amplitude modulation encoding (FAME) strategy transforms a fast-varying temporal fine structure into a slowly varying frequency modulation (FM) signal. Transformations are always based on center frequencies, and no transfer to a faster varying FM is implemented. Also no fitting to a patient specific range of stimulation rate is implemented.

SUMMARY OF THE INVENTION

Embodiments of the present invention are directed to a signal processing arrangement and corresponding method that generates electrode stimulation signals to electrode contacts in an implanted cochlear implant array. An input sound signal is processed to generate band pass signals that each represent a band pass channel defined by an associated band of audio frequencies. A characteristic envelope signal is extracted for each band pass signal based on its amplitude. Stimulation timing signals are generated for each band pass signal, including, for one or more selected band pass signals, using a timing function defined to: i. represent instantaneous frequency based on the band pass signal temporal fine structure features, ii. determine a mapped instantaneous frequency by adjusting the instantaneous frequency based on a frequency relation factor representing a relationship between: (1) the range of audio frequencies for the band pass channel of the selected band pass signal, and (2) a patient-specific, channel-specific range of stimulation rates defined based on patient-specific pitch perception measurements to enhance patient pitch perception within the range of audio frequencies for the band pass channel of the selected band pass signal, and iii. generate the stimulation timing signal for the selected band pass signal at the mapped instantaneous frequency of the selected band pass signal. The electrode stimulation signals are produced for each electrode contact based on the envelope signals and the stimulation timing signals.

In further specific embodiments, the patient-specific, channel-specific range of stimulation rates may be defined specifically to elicit monotonically increasing pitch perception measurements within the range of audio frequencies either for the band pass channel of the selected band pass signal, for multiple adjacent band pass channels, or for each of the band pass channels. In addition, the range of audio frequencies for the band pass channel of the selected band pass signal and the patient-specific, channel-specific range of stimulation rates may be matched such that there is a bijective relationship between the audio frequencies and the stimulation rates, in which case, a stretching/compressing algorithm may be applied.

The band pass signal temporal fine structure features used by the timing function may specifically include zero crossings of the band pass signal. The stimulation timing signals for the one or more selected band pass signals specifically may be Channel-Specific Sampling Sequences (CSSS). Extracting the characteristic envelope signals may include using low pass filters or Hilbert filters. The stimulation timing signals for some band pass signals may be generated without the timing function, using Continuous Interleaved Sampling (CIS) coding.

DETAILED DESCRIPTION OF SPECIFIC EMBODIMENTS

Prior art stimulation schemes rely on the principle that the coded stimulation signal presented to the cochlear implant user is deduced from a signal that a normal hearing person would receive in the same hearing situation. In particular, fundamental and higher harmonic frequencies are presented to the cochlear implant user in a comparable way as perceived by normal hearing persons. Embodiments of the present invention give this principle a lower priority and instead rely on the plasticity of the brain being able to retrieve distinct information from distinct signal patterns. In some circumstances the harmonic relations present in the input sound signal may be sacrificed in the coded stimulation signal that is presented to the cochlear implant user.

The existing FSP and FS4 coding approaches may be adapted to implement this idea. In embodiments of the present invention, stimulation timing signals are generated using a timing function defined to represent instantaneous frequency based on the temporal fine structure features. Then a mapped instantaneous frequency is derived by adjusting the instantaneous frequency based on a frequency relation factor that represents a relationship between the band pass range of audio frequencies and a patient-specific, channel-specific range of stimulation rates defined based on patient-specific pitch perception measurements to enhance patient pitch perception within the range of audio frequencies for the band pass channel. The stimulation timing signals are then generated at the mapped instantaneous frequency.

Figure 2A:
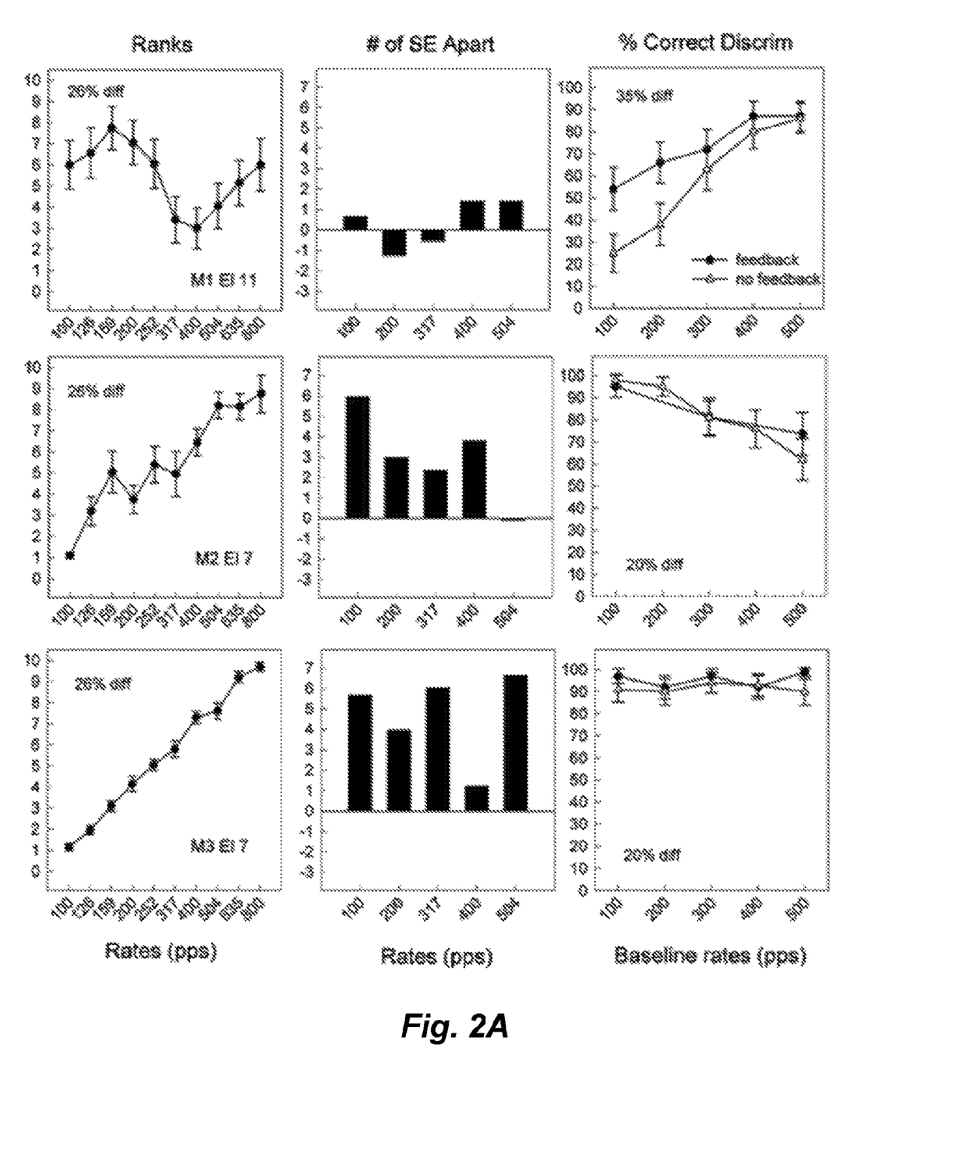
FIGS. 2A-2C show examples of pitch perception measurements for six different cochlear implant users.
Figure 2B:
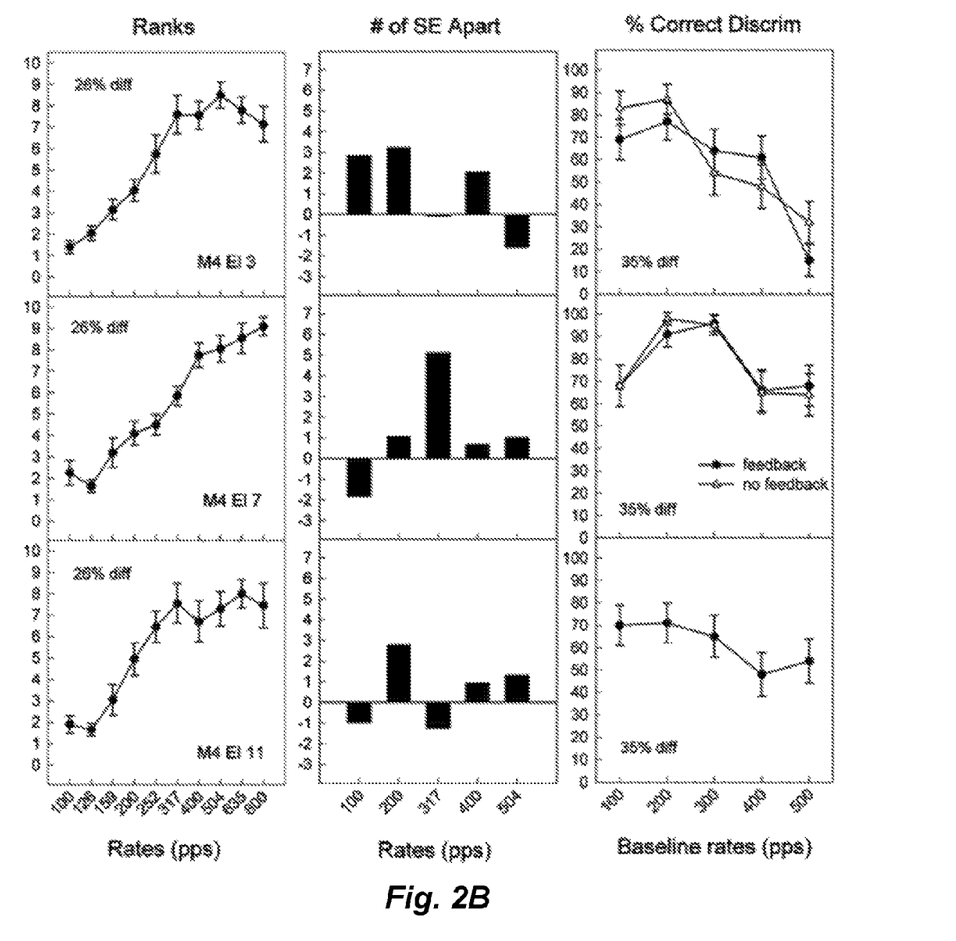
Figure 2C:
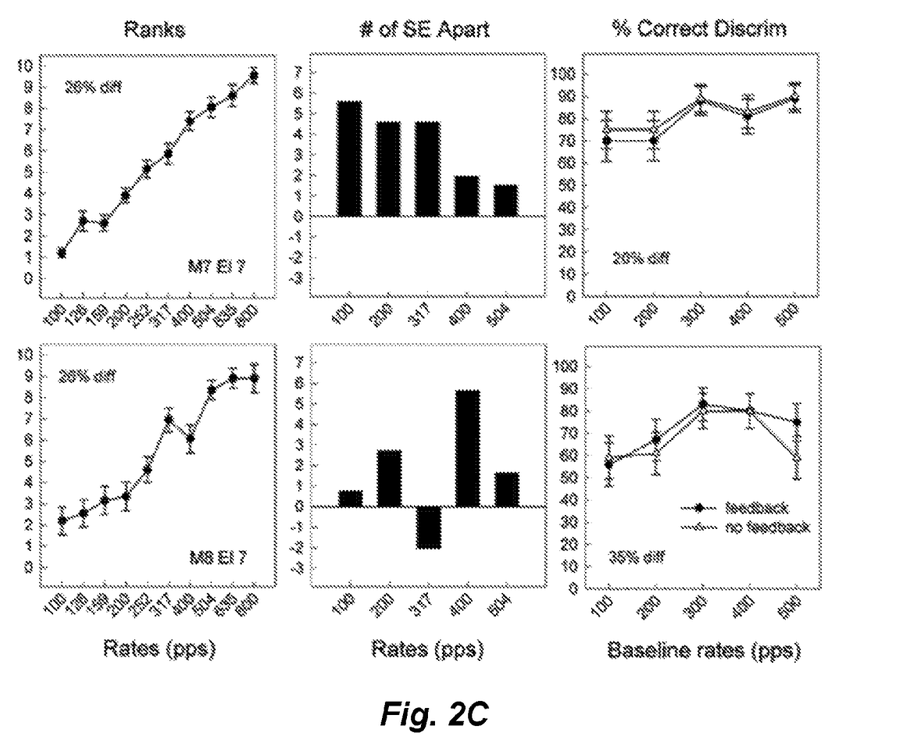

More specifically, a range of channel-specific stimulation rates (CSR) can be determined based on the observation that a given user's pitch perception for a given channel generally increases with increasing presented stimulation rate. For example, pitch perception measurements can be performed as described by Kong 2010, referenced above. FIGS. 2A-2C are from FIG. 1 of Kong 2010, for six different cochlear implant users. Results from individual subjects M1, M2, M3, M4, M7, and M8 are plotted in different rows. Subject M4 was tested on three different electrodes El 3, El 7, and El 11 and the results on individual electrodes are plotted separately.

The left panels in FIGS. 2A-2C show subjectively perceived pitch (on an arbitrary scale from 0 to 10) vs. the stimulation rate in pulses per second (pps). The general tendency shown is a higher pitch perception at higher presented stimulation rate. However, for some patients and for some stimulation electrodes, the perceived pitch is monotonically increasing over the entire presented range of stimulation rates, while in other cases there are one or more sub-regions where stimulation rates are perceived as lower pitches even though the presented stimulation rates were higher. In the former case, the entire range of stimulation rates can be defined as a patient-specific, channel-specific range of stimulation rates, also referred to as a unique range of stimulation rates (URSR). In the latter case, an appropriate portion of the pitch perception response range has to be selected as the URSR; for example, the longest monotonic sub-range, or the sub-range that best fits to the neighboring frequency channels as explained in more detail below. So in FIG. 1, for patient M1 electrode 11 (the top row in FIG. 2A), the URSR can be either 100-150 pps or 400-800 pps, as in either range, the pitch ranking provides monotonically increasing results. Likewise, for Patient M4, electrode 3 (the top row in FIG. 2B), the URSR will be 100-500 pps, while for electrode 7 (the middle row in FIG. 2B), the URSR will be 125-800 pps, etc. For electrode 7 of patient M7 (the top row in FIG. 2C), the entire range of stimulation rate measurements is monotonically increasing and can be used as the URSR.

The URSR defined for each band pass channel has to be mapped to the frequency bandwidth of the channel. For example, the URSR can be larger than the channel bandwidth, and a URSR compressing algorithm can be applied to match the corresponding channel bandwidth. More frequently, the URSR will be less than that of the corresponding channel, in which case a URSR stretching algorithm can be applied to match the channel bandwidth. As a result, each frequency of the input sound signal can be uniquely assigned to a specific channel dependent stimulation rate such that the range of audio frequencies for the band pass channel of the selected band pass signal and the patient-specific, channel-specific range of stimulation rates are matched with a bijective relationship between the audio frequencies and the stimulation rates. For example, given a band pass channel with a lower frequency of 500 Hz and an upper frequency of 750 Hz, and the patient-specific URSR for this channel corresponding to 100-500 pps, then the frequency range of 500-750 Hz will be mapped so that a 100 pps stimulation pulse rate corresponds to a sensed 500 Hz tone, and 500 pps stimulation pulse rate will be mapped for a 750 Hz sensed tone. A linear relationship may be imposed for the mapped pulse rates between the lower and upper frequencies of the band pass channel. This stretching/compressing algorithm may adversely affect the preservation of harmonics present in the input sound signal. But, as explained previously, this approach primarily relies on the adaptability of the human brain to retrieve unique information out of a unique signal.

Figure 3:
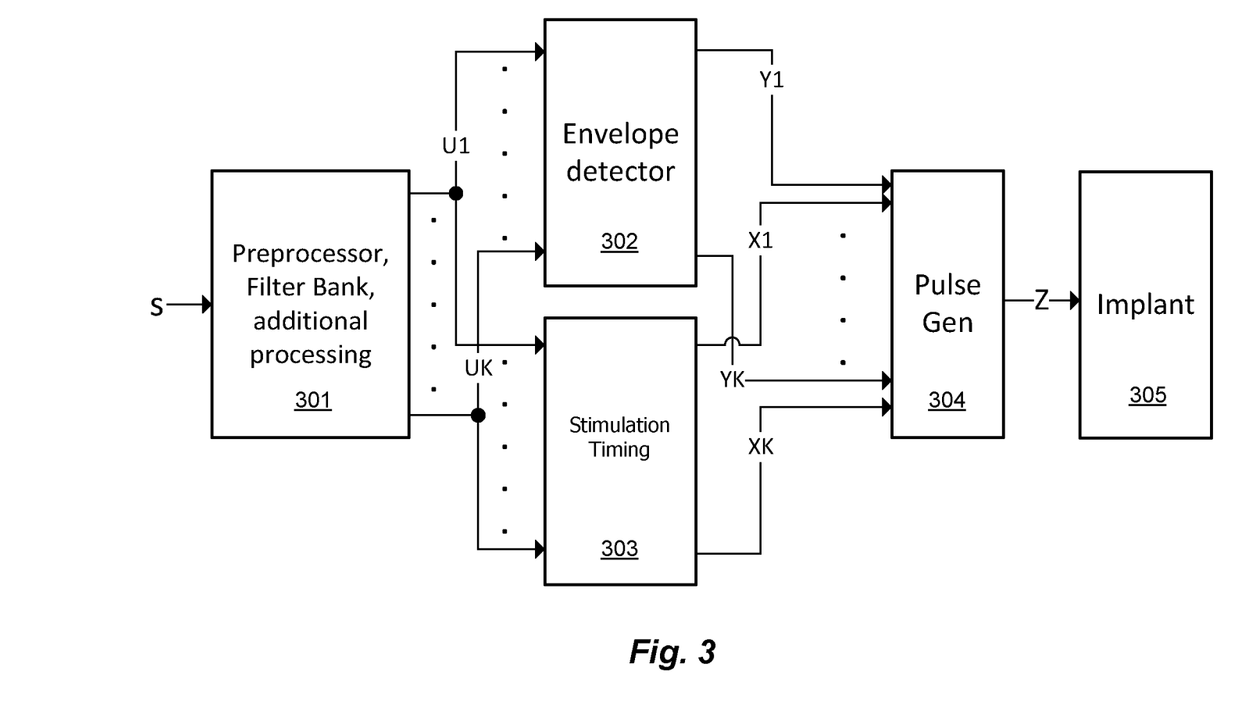
FIG. 3 shows various functional blocks in a signal processing arrangement for a hearing implant according to an embodiment of the present invention.
Figure 4:
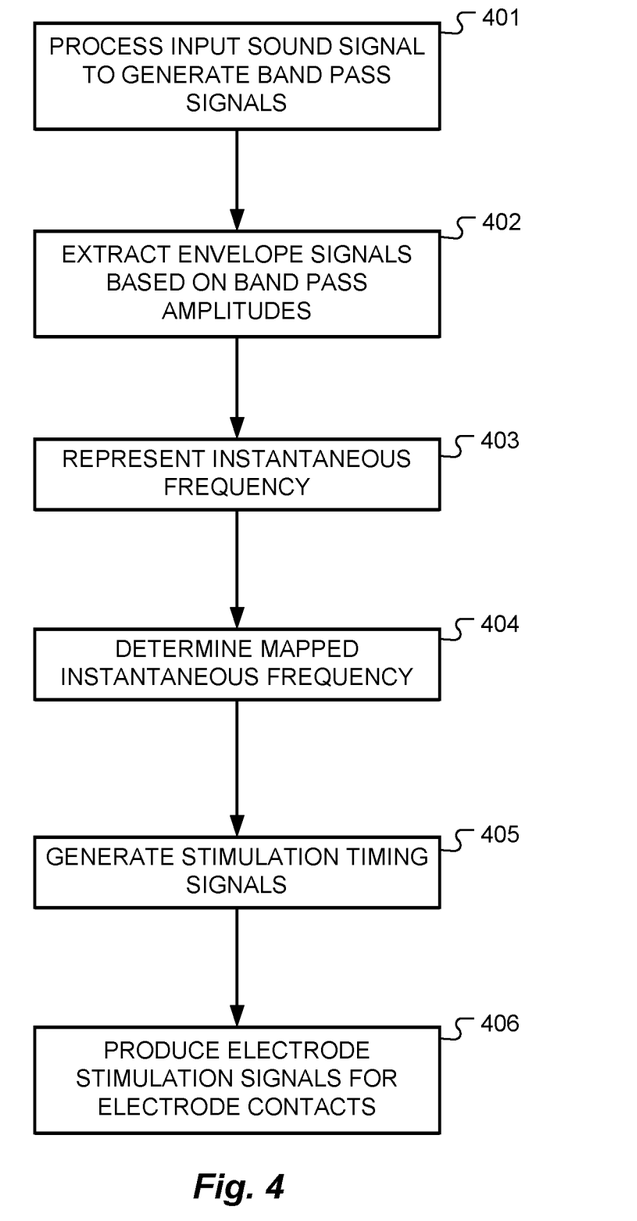
FIG. 4 shows various logical steps in developing electrode stimulation signals according to an embodiment of the present invention.

FIG. 3 shows various functional blocks in a signal processing arrangement for a hearing implant and FIG. 4 is a flow chart showing various logical steps in producing electrode stimulation signals to electrode contacts in an implanted cochlear implant array according to an embodiment of the present invention. A pseudo code example of such a method can be set forth as:

```
Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
        InstantaneousFreq (band_pass_signals, inst_freq)
        MappedFreq (inst_freq, mapped_freq)
        TimingGen (mapped_freq, stim_timing)
Pulse Generation:
    PulseGenerate (band_pass_envelopes, stim_timing, out_pulses)
```

The details of such an arrangement are set forth in the following discussion.

In the arrangement shown in FIG. 3, the initial input sound signal is produced by one or more sensing microphones, which may be omnidirectional and/or directional. Preprocessor Filter Bank 301 pre-processes this input sound signal, step 401, with a bank of multiple parallel band pass filters, each of which is associated with a specific band of audio frequencies; for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of the Preprocessor Filter Bank 301 can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as automatic gain control (AGC) and/or noise reduction.

Figure 5:
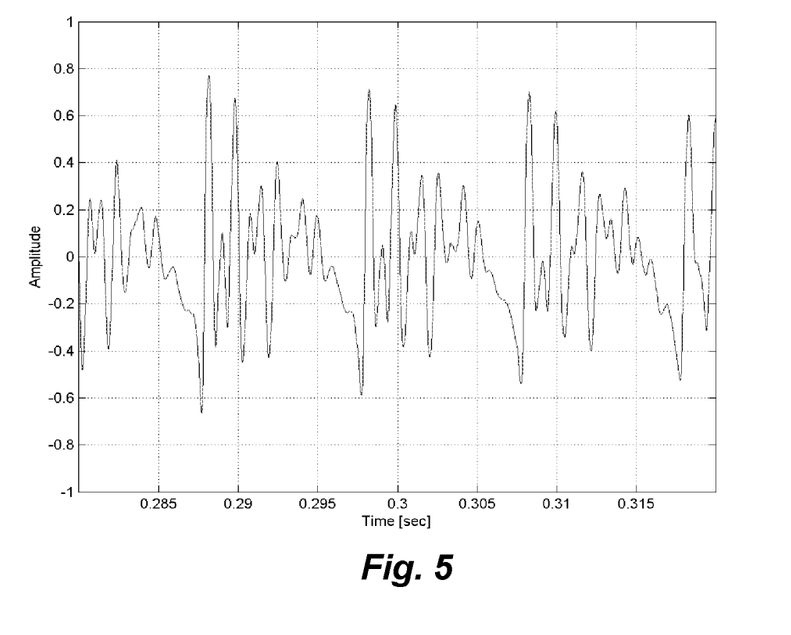
FIG. 5 shows an example of a short time period of an audio speech signal from a microphone.
Figure 6:
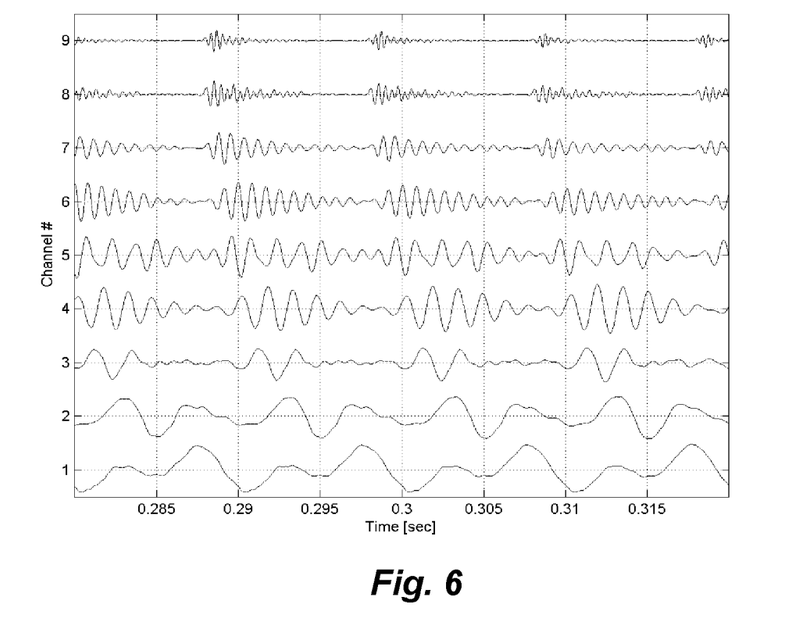
FIG. 6 shows an acoustic microphone signal decomposed by band-pass filtering by a bank of filters into a set of band pass signals.

FIG. 5 shows an example of a short time period of an input speech signal from a sensing microphone, and FIG. 6 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels - 1 do
    for s = 0 to number of samples - 1 do
        Y_j(s) = B_{0j} * X_j(s) + Z_{0j}
        for i = 0 to order - 3 do
            Z_{ij} = B_{i+1,j} * X_j(s) + Z_{i+1,j} - A_{i+1,j} * Y_j(s)
        end for
        Z_{order-2,j} = B_{order-1,j} * X_j(s) - A_{order-1,j} * Y_j(s)
    end for
end for
```

The band pass signals $U_1$ to $U_K$ (which can also be thought of as electrode channels) are output to an Envelope Detector 302 and a Stimulation Timing Module 303. The Envelope Detector 302 extracts characteristic envelop signals outputs $Y_1, \ldots, Y_K$, step 402, that represent the channel-specific band pass envelopes. The envelope extraction can be represented by $Y_k = LP(|U_k|)$, where $|.|$ denotes the absolute value and $LP(.)$ is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

The Stimulation Timing Module 303 processes selected temporal fine structure features of the band pass signals $U_1, \ldots, U_K$ such as negative-to-positive zero crossings to generate stimulation timing signals $X_1, \ldots, X_K$, using specially defined timing and mapping functions. In the following discussion, the band pass signals $U_1, \ldots, U_K$ are assumed to be real valued signals, so in the specific case of an analytic orthogonal filter bank, the Stimulation Timing Module 303 considers only the real valued part of $U_k$.

For one or more selected band pass signals, the Stimulation Timing Module 303 represents instantaneous frequency of the band pass signal based on the temporal fine structure features, step 403. Specifically, the Stimulation Timing Module 303 may analyze the zero crossings of the band pass signal (negative-to-positive transitions of the signal value), and based on the temporal distance $\Delta t_0$ between succeeding zero-crossings, the instantaneous frequency $f_0 = 1/\Delta t_0$ can be computed. The temporal distance $\Delta t_0$ relative to the preceding zero-crossing can be determined with the help of a memory element in the Stimulation Timing Module 303. In some embodiments, the Stimulation Timing Module 303 may limit the instantaneous band pass frequency $f_0$ to the upper and lower frequency boundaries $f_{L1}$ and $f_{U1}$ of the respective filter band. For example, the band pass signal of electrode 4 as above may have a lower frequency boundary $f_{L1}$ of 500 Hz and an upper frequency boundaries of $f_{U1}$=750 Hz, and the patient specific URSR may be from $f_{L2}$=100 Hz (or pps) to $f_{U2}$=500 Hz (or pps).

Once the Stimulation Timing Module 303 has determined the instantaneous frequency of the band pass signal, it then determines a mapped instantaneous frequency by adjusting the instantaneous frequency based on a frequency relation factor that represents a relationship between: (1) the range of audio frequencies for the band pass channel of the selected band pass signal, and (2) a patient-specific, channel-specific range of stimulation rates defined based on patient-specific pitch perception measurements to enhance patient pitch perception within the range of audio frequencies for the band pass channel of the selected band pass signal, step 404. Continuing with the previous example of electrode 4, a frequency relation factor r can be computed by $r=(f_{U2}-f_{L2})/(f_{U1}-f_{L1})=1.6$. The patient-specific mapped instantaneous frequency $f_m$ with $f_{L2} \le f_m \le f_{U2}$ can then be computed from the instantaneous frequency $f_0$ with $f_{L1} \le f_0 \le f_{U1}$ by $f_m = f_{L2} + r^*(f_0 - f_{U2})$.

The patient-specific, channel-specific range of stimulation rates may be defined specifically to elicit monotonically increasing pitch perception measurements within the range of audio frequencies either just for the band pass channel of the selected band pass signal, or for multiple adjacent band pass channels, or for each of the band pass channels. The Stimulation Timing Module 303 then generates the stimulation timing signals for the selected band pass signal at the mapped instantaneous frequency of the selected band pass signal, step 405. For instance, the stimulation timing signals may specifically be Channel-Specific Sampling Sequences (CSSS).

Where $\Delta t_0$ denotes the time interval between zero crossings in the band pass signal, and $\Delta t_m$ refers to the mapped time interval between applied stimulation pulses Stimulation Timing Module 303 can compute $\Delta t_m = 1/f_m$. This mapped time interval always refers to the last applied stimulation pulse on the relevant channel. When the stimulation initially starts, then the very first pulse will not be modified in timing and serves as a starting reference. Alternatively, the mapping also can be performed using real-time frequency shifting methods in the time domain such as described in Juillerat, Nicolas, Simon Schubiger-Banz, and Stefan Müller Arisona. "Low latency audio pitch shifting in the time domain." *Audio, Language and Image Processing, 2008. ICALIP 2008. International Conference on*. IEEE, 2008 (incorporated herein by reference in its entirety) and Haghparast, Azadeh, Henri Penttinen, and Vesa Välimäki. "Real-time pitchshifting of musical signals by a time-varying factor using normalized filtered correlation time-scale modification (NFC-TSM)." *Proc. of the DAFx*. 2007 (incorporated herein by reference in its entirety), or by block processing orientated pitch shifting methods in the frequency domain based on phase vocoders such as described in Nie, Kaibao, Ginger Stickney, and Fan-Gang Zeng. "Encoding frequency modulation to improve cochlear implant performance in noise." *Biomedical Engineering, IEEE Transactions on* 52.1 (2005): 64-73 (incorporated herein by reference in its entirety). The stimulation timing signals for some band pass signals may be generated without the timing function, using Continuous Interleaved Sampling (CIS) coding.

The extracted signal envelopes $Y_1, \ldots, Y_K$ from the Envelope Detector 302, and the stimulation timing signals $X_1, \ldots, X_K$ from the Stimulation Timing Module 303 are input signals to a Pulse Generator 304 that produces the electrode stimulation signals Z for the electrode contacts in the implanted electrode array 305, step 406. The Pulse Generator 304 applies a patient-specific mapping function—for example, using instantaneous nonlinear compression of the envelope signal (map law)—that is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals.

Figure 7A:
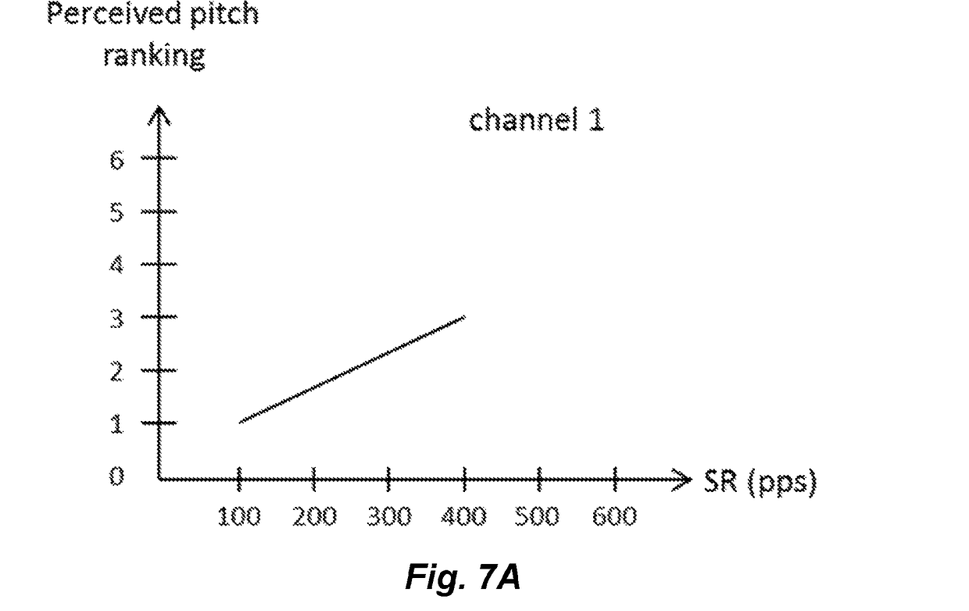
FIG. 7A-7D show graphs that illustrate how pitch perception may be monotonically increasing across multiple band pass channels.
Figure 7B:
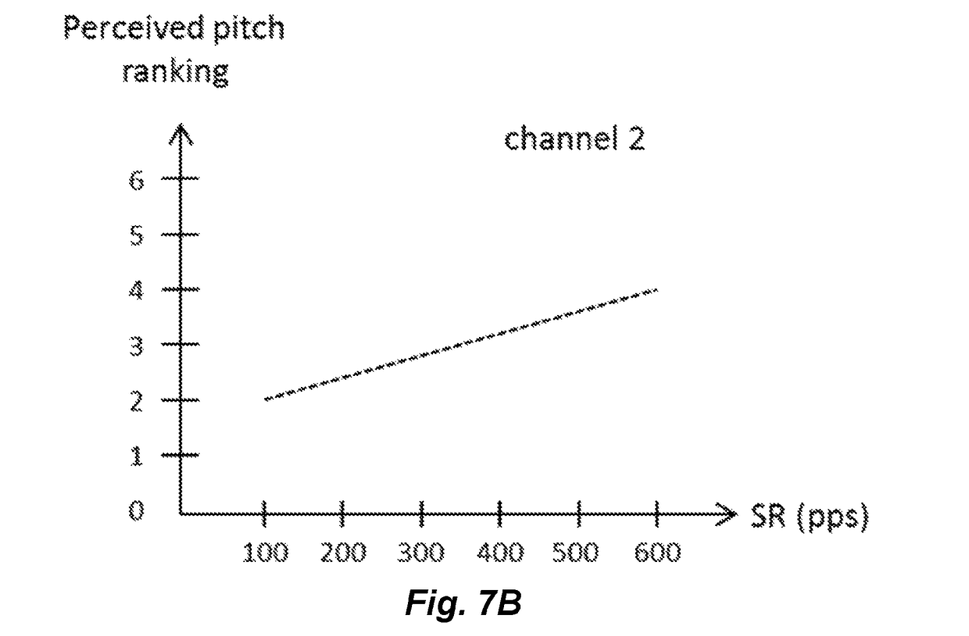
Figure 7C:
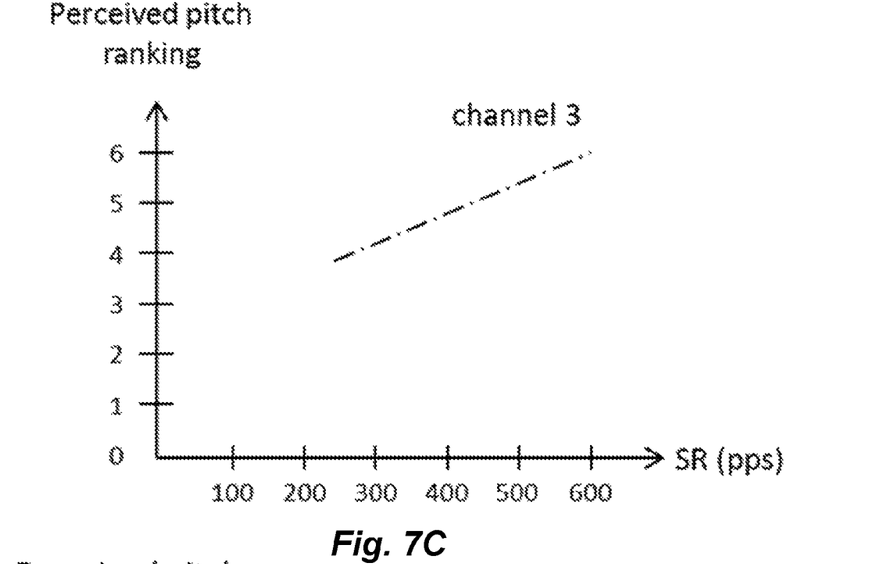
Figure 7D:
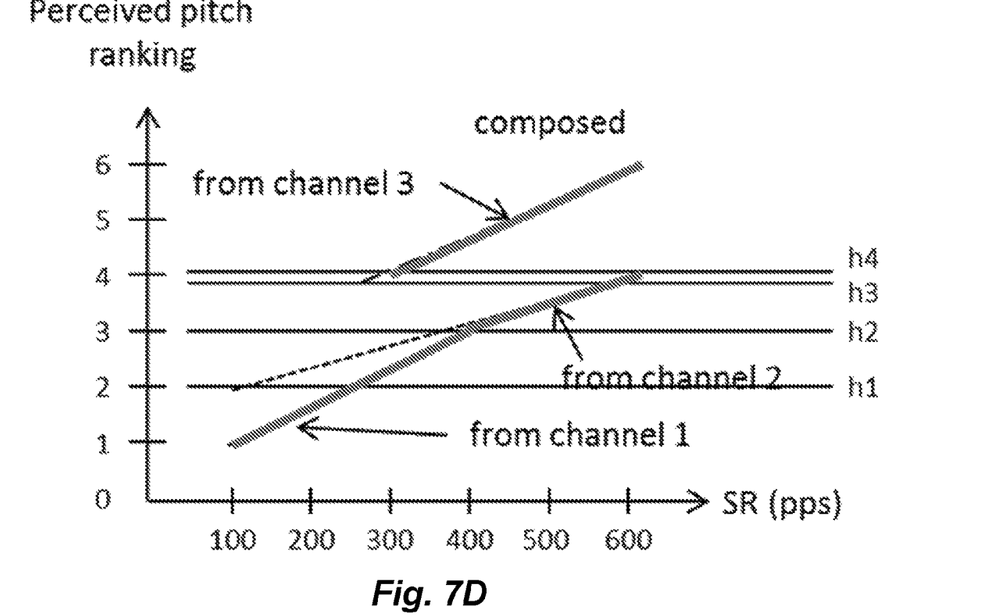
Figure 8A:
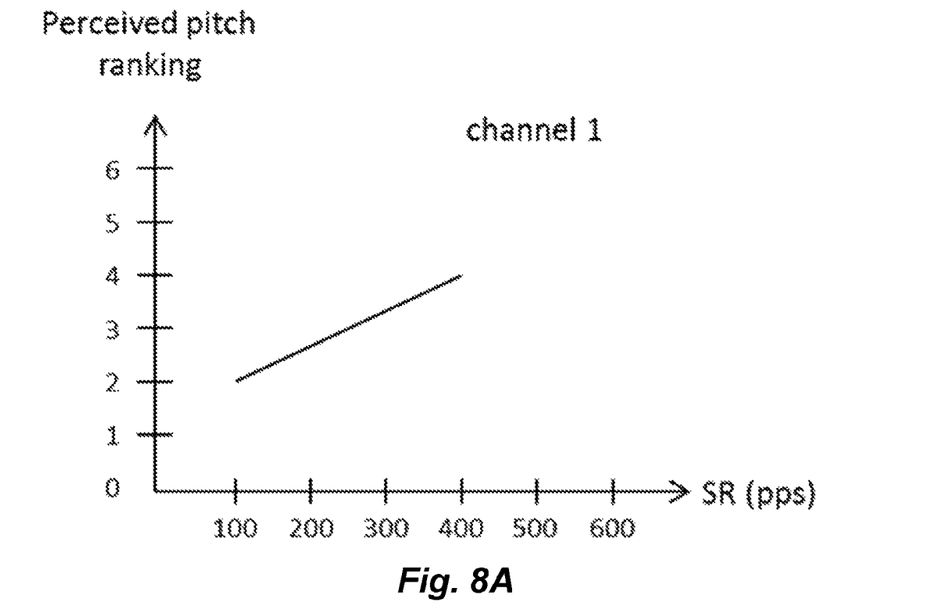
FIG. 8A-8D show another example of graphs that illustrate how pitch perception may be monotonically increasing across multiple band pass channels.
Figure 8B:
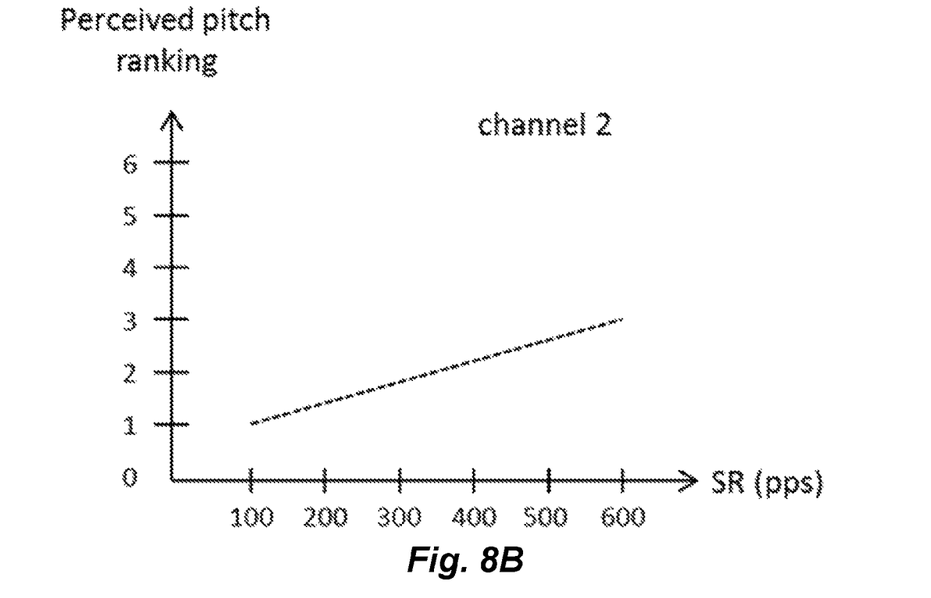
Figure 8C:
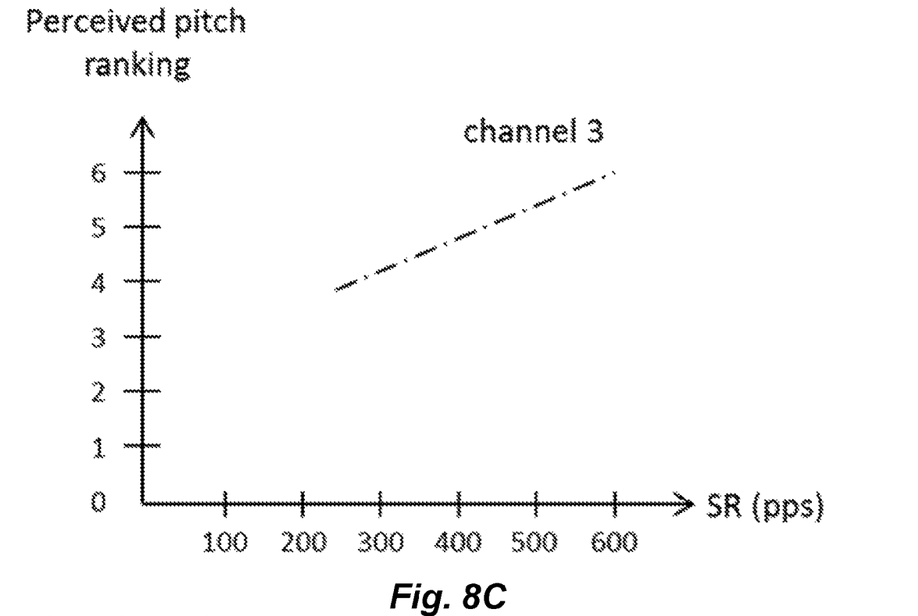
Figure 8D:
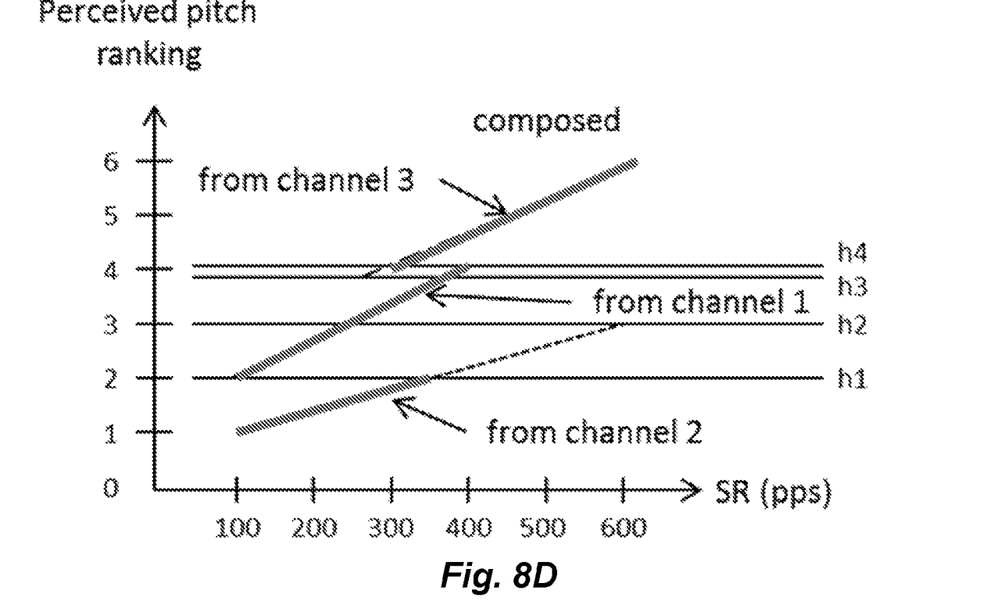

In some embodiments, there may usefully be a further requirement that the pitch perception should not only be monotonically increasing within each band pass channel, but also monotonically increasing over the entire frequency range of all channels, which typically is from 100 Hz to about 8 kHz. A typical scenario is shown in FIGS. 7A-7D. FIGS. 7A-7C show the three URSR for the channels 1-3. In this case, the same stimulation rate causes lower pitch perception in channel 1 than in channels 2 and 3 and also lower pitch perception in channel 2 than in channel 3. However, the perceived pitch rankings overlap (it is assumed here that the y-axes are comparable among each other). In order to achieve a monotonic "perceived pitch ranking" over a combination of channels 1-3, only selected portions of the individual URSRs can be used. As shown in FIG. 7D, the entire URSR of channel 1 can be combined with the portion h2-h4 from channel 2 and the portion from channel 3 above h4. Alternatively, the portion from channel 1 up to h1 can be combined with h2-h3 from channel 2 plus the entire URSR from channel 3, etc.

FIGS. 8A-8D show that this strategy even can be applied to users who have very unnatural pitch perceptions. In this example, the pitch perception (or perceived pitch ranking) in channel 2 is lower than in channel 1 for the same stimulation rate. Consequently, in the composed FIG. 8D, the lowest pitch perception is related to the signal on channel 2. The entire pitch ranking may be composed, for example, from the URSR from channel 2 to up to h1 together with the entire URSR from channel 1 and the URSR from channel 3 starting at h4. However, this inverted order of channels 1 and 2 also requires that the URSR of channel 2 has to be matched to the bandwidth of channel 1 and vice versa as well as the band pass signal applied to channel 1 (after splitting the input sound signal into a plurality of band pass signals) has to be re-applied to channel 2 and vice versa.

Thus, embodiments of the present invention can offer better usage of the stimulation pulse rate and better frequency discrimination than in prior approaches. On the other hand, the harmonic relations of frequency components in the input signal can become distorted or lost.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for generating electrode stimulation signals to electrode contacts in an implanted cochlear implant electrode array, the method comprising:
    processing an input sound signal to generate a plurality of band pass signals, wherein each band pass signal represents a band pass channel defined by an associated range of audio frequencies, and wherein each band pass signal has characteristic amplitude and temporal fine structure features;
    extracting a characteristic envelope signal for each band pass signal based on its amplitude;
    generating stimulation timing signals for each band pass signal, wherein for each of one or more selected band pass signals, the stimulation timing signals are generated based on a timing function defined to:
        i. represent instantaneous frequency based on the band pass signal temporal fine structure features,
        ii. determine a mapped instantaneous frequency by adjusting the instantaneous frequency based on a frequency relation factor representing a relationship between:
            (1) the range of audio frequencies for the band pass channel of the selected band pass signal, and
            (2) a patient-specific, channel-specific range of stimulation rates defined based on patient-specific pitch perception measurements to enhance patient pitch perception within the range of audio frequencies for the band pass channel of the selected band pass signal, and
        iii. generate the stimulation timing signal for the selected band pass signal at the mapped instantaneous frequency of the selected band pass signal; and
    producing the electrode stimulation signals for each electrode contact based on the envelope signals and the stimulation timing signals.

2. The method according to claim 1, wherein the patient-specific, channel-specific range of stimulation rates is defined to elicit monotonically increasing pitch perception measurements within the range of audio frequencies for the band pass channel of the selected band pass signal.

3. The method according to claim 1, wherein the patient-specific, channel-specific range of stimulation rates is defined to elicit monotonically increasing pitch perception measurements within the range of audio frequencies for a plurality of adjacent band pass channels.

4. The method according to claim 1, wherein the patient-specific, channel-specific range of stimulation rates is defined to elicit monotonically increasing pitch perception measurements within the range of audio frequencies for each of the band pass channels.

5. The method according to claim 1, wherein the range of audio frequencies for the band pass channel of the selected band pass signal and the patient-specific, channel-specific range of stimulation rates are matched such that there is a bijective relationship between the audio frequencies and the stimulation rates.

6. The method according to claim 5, wherein a stretching/compressing algorithm is applied.

7. The method according to claim 1, wherein the band pass signal temporal fine structure features used by the timing function include zero crossings of the band pass signal.

8. The method according to claim 1, wherein stimulation timing signals for the one or more selected band pass signals are Channel-Specific Sampling Sequences (CSSS).

9. The method according to claim 1, wherein extracting the characteristic envelope signals includes using low pass filters.

10. The method according to claim 1, wherein extracting the characteristic envelope signals includes using Hilbert filters.

11. The method according to claim 1, wherein stimulation timing signals for a plurality band pass signals are generated without the timing function, using Continuous Interleaved Sampling (CIS) coding.

12. A system for generating electrode stimulation signals to electrode contacts in an implanted cochlear implant electrode array, the arrangement comprising:
    a preprocessor filter bank configured to process an input sound signal to generate a plurality of band pass signals, wherein each band pass signal represents a band pass channel defined by an associated band of audio frequencies, and wherein each band pass signal has a characteristic amplitude and temporal fine structure features;
    an envelope detector configured to extract a characteristic envelope signal for each band pass signal based on its amplitude;
    a stimulation timing module configured to generate stimulation timing signals for each band pass signal, wherein for each of one or more selected band pass signals, the stimulation timing module generates the stimulation timing signals based on a timing function defined to:
        i. represent instantaneous frequency based on the band pass signal temporal fine structure features, and
        ii. determine a mapped instantaneous frequency by adjusting the instantaneous frequency based on a frequency relation factor representing a relationship between:
            (1) the range of audio frequencies for the band pass channel of the selected band pass signal, and
            (2) a patient-specific, channel-specific range of stimulation rates defined based on patient-specific pitch perception measurements to enhance patient pitch perception within the range of audio frequencies for the band pass channel of the selected band pass signal, and
        iii. generate the stimulation timing signal for the selected band pass signal at the mapped instantaneous frequency of the selected band pass signal; and
    a pulse generator configured to produce the electrode stimulation signals for each electrode contact based on the envelope signals and the stimulation timing signals.

13. The system according to claim 12, wherein the stimulation timing module is configured to use a timing function in which the patient-specific, channel-specific range of stimulation rates is defined to elicit monotonically increasing pitch perception measurements within the range of audio frequencies for the band pass channel of the selected band pass signal.

14. The system according to claim 12, wherein the patient-specific, channel-specific range of stimulation rates is defined to elicit monotonically increasing pitch perception measurements within the range of audio frequencies for a plurality of adjacent band pass channels.

15. The system according to claim 12, wherein the stimulation timing module is configured to use a timing function in which the patient-specific, channel-specific range of stimulation rates is defined to elicit monotonically increasing pitch perception measurements within the range of audio frequencies for each of the band pass channels.

16. The system according to claim 12, wherein the stimulation timing module is configured to match the range of audio frequencies for the band pass channel of the selected band pass signal and the patient-specific, channel-specific range of stimulation rates such that there is a bijective relationship between the audio frequencies and the stimulation rates.

17. The system according to claim 16, wherein the stimulation timing module applies a stretching/compressing algorithm.

18. The system according to claim 12, wherein the stimulation timing module is configured to use a timing function in which the fine structure detector uses a timing function in which the band pass signal temporal fine structure features include zero crossings of the band pass signal.

19. The system according to claim 12, wherein the stimulation timing module is configured to use Channel-Specific Sampling Sequences (CSSS) to generate the stimulation timing signals.

20. The system according to claim 12, wherein the envelope detector is configured to use low pass filters for extracting the characteristic envelope signals.

21. The system according to claim 12, wherein the envelope detector is configured to use Hilbert filters for extracting the characteristic envelope signals.

22. The system according to claim 12, wherein the stimulation timing module is further configured to generate stimulation timing signals for a plurality band pass signals without the timing function, using Continuous Interleaved Sampling (CIS) coding.

23. A non-transitory tangible computer-readable medium having instructions thereon for generating electrode stimulation signals to electrode contacts in an implanted cochlear implant electrode array, the instructions comprising:

processing an input sound signal to generate a plurality of band pass signals, wherein each band pass signal represents a band pass channel defined by an associated range of audio frequencies, and wherein each band pass signal has a characteristic amplitude and temporal fine structure features;

extracting a characteristic envelope signal for each band pass signal based on its amplitude;

generating stimulation timing signals for each band pass signal, wherein for each of one or more selected band pass signals, the stimulation timing signals are generated based on a timing function defined to:

i. represent instantaneous frequency based on the band pass signal temporal fine structure features, ii. determine a mapped instantaneous frequency by adjusting the instantaneous frequency based on a frequency relation factor representing a relationship between:

(1) the range of audio frequencies for the band pass channel of the selected band pass signal, and (2) a patient-specific, channel-specific range of stimulation rates defined based on patient-specific pitch perception measurements to enhance patient pitch perception within the range of audio frequencies for the band pass channel of the selected band pass signal, and iii. generate the stimulation timing signal for the selected band pass signal at the mapped instantaneous frequency of the selected band pass signal; and producing the electrode stimulation signals for each electrode contact based on the envelope signals and the stimulation timing signals.

\* \* \* \* \*